United States Patent
Jeong et al.

(10) Patent No.: US 12,234,215 B2
(45) Date of Patent: Feb. 25, 2025

(54) CARBONATE COMPOUND CONTAINING FLUOROSULFONYL GROUP, AND PREPARATION METHOD AND USE OF SAME

(71) Applicant: SAMHWA PAINTS INDUSTRIES CO., LTD., Gyeonggi-do (KR)

(72) Inventors: Yuri Jeong, Gyeonggi-do (KR); Myengchan Hong, Gyeonggi-do (KR); Chongyun Kwak, Seoul (KR)

(73) Assignee: SAMHWA PAINTS INDUSTRIES CO., LTD., Gyeonggi-do (KR)

( * ) Notice: Subject to any disclaimer, the term of this patent is extended or adjusted under 35 U.S.C. 154(b) by 712 days.

(21) Appl. No.: 17/610,997

(22) PCT Filed: Jun. 23, 2020

(86) PCT No.: PCT/KR2020/008182
§ 371 (c)(1),
(2) Date: Nov. 12, 2021

(87) PCT Pub. No.: WO2020/262947
PCT Pub. Date: Dec. 30, 2020

(65) Prior Publication Data
US 2022/0220092 A1    Jul. 14, 2022

(30) Foreign Application Priority Data

Jun. 24, 2019 (KR) .................. 10-2019-0075152

(51) Int. Cl.
*C07D 317/36* (2006.01)
*H01M 10/052* (2010.01)
*H01M 10/0567* (2010.01)

(52) U.S. Cl.
CPC ........ *C07D 317/36* (2013.01); *H01M 10/052* (2013.01); *H01M 10/0567* (2013.01)

(58) Field of Classification Search
CPC .............. C07D 317/36; H01M 10/052; H01M 10/0567
See application file for complete search history.

(56) References Cited

U.S. PATENT DOCUMENTS

| 8,853,448 | B2 | 10/2014 | Sanchez et al. |
| 2010/0174113 | A1 | 7/2010 | Sanchez et al. |

FOREIGN PATENT DOCUMENTS

| JP | 20080120690 A2 | 5/2008 |
| KR | 20080026522 A | 3/2008 |
| KR | 00000867535 B1 | 11/2008 |
| KR | 20100056672 A | 5/2010 |
| KR | 00001020465 B1 | 3/2011 |
| KR | 20120045027 A | 5/2012 |
| KR | 20140139906 A | 12/2014 |
| KR | 20160029065 A | 3/2016 |
| KR | 00001736739 B1 | 5/2017 |

OTHER PUBLICATIONS

Mohanty et al. "Topologically Reversible Transformation of Tricyclic Polymer into Polyring Using Disulfide/Thiol Redox Chemistry." Macromolecules 51(14): 5313-5322 Jul. 11, 2018.

*Primary Examiner* — Alicia L Otton
(74) *Attorney, Agent, or Firm* — Nixon Peabody LLP; David S. Resnick; Ravinderjit S. Braich

(57) ABSTRACT

The present invention relates to a novel fluorosulfonyl carbonate compound. The present invention also relates to a method of preparing the fluorosulfonyl carbonate compound. The present invention also relates to an electrolyte additive for a secondary battery comprising the fluorine-containing carbonate compound, an electrolyte and a secondary battery using the same. The present invention also relates to a pharmaceutical intermediate or polymer compound prepared using the fluorosulfonyl carbonate compound.

17 Claims, No Drawings

CARBONATE COMPOUND CONTAINING FLUOROSULFONYL GROUP, AND PREPARATION METHOD AND USE OF SAME

TECHNICAL FIELD

The present invention relates to a carbonate compound containing a novel fluorosulfonyl group and a preparation method and use thereof.

CROSS REFERENCE TO RELATED APPLICATIONS

This Application is a 371 National Phase Entry of International Patent Application No. PCT/KR2020/008182 filed Jun. 23, 2020, which claims the benefit under 35 U.S.C. § 119 (b) of Korean Patent Application No. 10-2019-0075152 filed Jun. 24, 2019, the contents of which are incorporated herein in their entirety by reference.

BACKGROUND

Each year, about 15,000 to 20,000 tons of electrolyte used in lithium ion batteries (LIBs) are being produced worldwide. If there is not significant improvement in performance through the production of electrolytes with well-established structures in industrial terms, it is difficult to expect any changes while maintaining the current status quo. If any battery performance improvement can be achieved by adding small amounts of components without structural replacement, the expectations are high in terms of more economical and efficient. For this reason, over the past several years, researchers are working on the synthesis of various electrolyte additives.

A solid electrolyte interphase (SEI) formed on a negative electrode of a secondary battery plays an important role in determining the performance of the battery such as irreversible capacity, shelf life, and safety. The SEI formation and growth causes progressively less contact in the component negative electrode, increasing the impedance in a cell. In addition, lithium plating reacts with an electrolyte and accelerates aging. The most successful additive used today for the purpose of preventing this phenomenon is vinylene carbonate (VC), but in the case of electric vehicles requiring high power, an electrochemical window of VC is narrow and is not suitable for applications. For this reason, various additives are under development.

SUMMARY OF INVENTION

Technical Problem

An object of the present invention is to provide a carbonate compound containing a fluorosulfonyl group.

Another object of the present invention is to provide a method of preparing the carbonate compound containing a fluorosulfonyl group.

Another object of the present invention is to provide an electrolyte additive for a secondary battery containing the carbonate compound containing a fluorosulfonyl group, an electrolyte for a lithium ion secondary battery, and a lithium ion secondary battery.

Another object of the present invention is to provide a pharmaceutical intermediate or a polymer compound produced by using the carbonate compound containing a fluorosulfonyl group.

Solution to Problem

In order to solve the above objects, the present invention provides a fluorosulfonyl carbonate compound represented by the following Formula 1; the method of preparing the compound includes the following steps:

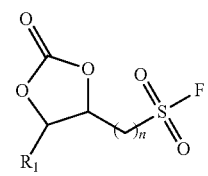

[Formula 1]

(S1) preparing a compound represented by the following Formula 3 from a compound represented by the following Formula 2;

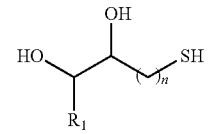

[Formula 2]

(S2) preparing a compound represented by the following Formula 4 from the compound represented by the following Formula 3;

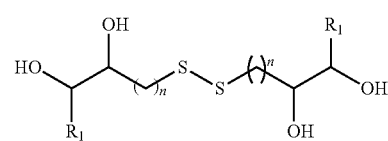

[Formula 3]

(S3) preparing a compound represented by Formula 1 from the compound represented by the Formula 4.

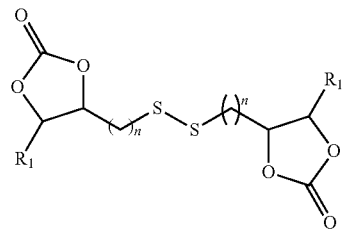

[Formula 4]

where, $R_1$ is each independently hydrogen, a halogen atom, an unsubstituted $C_1$-$C_{10}$ alkyl group, or a halogen-substituted $C_1$-$C_{10}$ alkyl group; and n is an integer of 1 to 5.

At this time, the step (S3) may further include preparing a compound represented by the following Formula 5 from the compound represented by the Formula 4; and the step (S4) may further include preparing the compound represented by the Formula 1 from the compound represented by the following Formula 5.

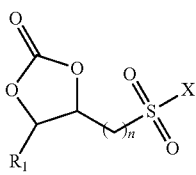

[Formula 5]

where, $R_1$ is each independently hydrogen, a halogen atom, an unsubstituted $C_1$-$C_{10}$ alkyl group, or a halogen-substituted $C_1$-$C_{10}$ alkyl group; X is Cl, Br or I; and n is an integer of 1 to 5.

The step (S1) may be carried out in the presence of an oxidizing agent, and in an embodiment of the present invention, hydrogen peroxide ($H_2O_2$) may be used as the oxidizing agent, but is not limited thereto.

The step (S2) may be carried out in the presence of any one or more selected from the group consisting of bis (trichloromethyl) carbonate, carbonyl chloride, carbonyl bromide, bis halo formate, diphenyl carbonate, dimethyl carbonate, diethyl carbonate, carbon dioxide, and di-2-pyridinol carbonate; and an organic solvent selected from dichloromethane, dichloroethane, chloroform, methanol, ethanol, dioxane, ethylene glycol, acetonitrile, tetrahydrofuran, toluene and dimethylformamide.

The step (S3) may be carried out in the presence of an electrophilic fluorinating agent, which may be a Selectfluor or N-fluorobenzenesulfonimide. By causing the compound represented by the above Formula 4 to react with the above electrophilic fluorinating agent, it is possible to directly prepare the above Formula 1 without preparing the above Formula 5.

Alternatively, in the step (S3), the disulfide of the compound represented by the Formula 4 may be subjected to an oxidation and halogenation reaction, and the step (S3) may be carried out by preparing the compound represented by the Formula 5 in the presence of at least one oxidizing agent selected from the group consisting of 1,3-dichloro-5,5-dimethylhydantoin (DCDMH), N-chlorosuccinimide (NCS), trimethylsilylchloride (TMSCl), cyanuric chloride, sodium hypochlorite (NaOCl), potassium peroxy monosulfate (Oxone), trichloroisocyanuric acid (TCCA), and N-bromosuccinimide (NBS).

The step (S4) may be carried out in the presence of any one or more selected from the group consisting of potassium fluoride, potassium difluoride, a Selectfluor, hydrofluoric acid, cesium fluoride, and N-fluorobenzenesulfonimide.

The present invention also provides an electrolyte additive for a secondary battery containing a fluorosulfonyl carbonate compound.

The present invention also provides an electrolyte containing the electrolyte additive for a secondary battery.

The present invention also provides a lithium secondary battery containing the electrolyte.

The present invention also provides a pharmaceutical intermediate or polymer compound prepared by using the fluorosulfonyl carbonate compound.

Advantageous Effects of Invention

The present invention provides a novel fluorosulfonyl carbonate compound represented by the Formula 1, and the compound of the present invention can be used as an electrolyte additive for a lithium secondary battery. In addition, a lithium secondary battery electrolyte containing an electrolyte additive containing the compound of the present invention, and a lithium secondary battery produced using the same have excellent life characteristics, storage characteristics, and thermal stability, and exhibit high charge/discharge efficiency, and thus have an effect of improving battery performance.

The fluorosulfonyl carbonate compound of the present invention can be variously utilized in the fields of pharmaceutical intermediates, preparation of polymer compounds and fine chemistry.

In addition, the method of preparing a fluorosulfonyl carbonate compound of the present invention is carried out as a simple and mild reaction process, can be produced with a fluorosulfonyl carbonate compound in high yield, and thus is also suitable for mass production.

DESCRIPTION OF EMBODIMENTS

The present invention will be described in detail below.

Although the description of the constituent elements which will be described below may be provided based on typical embodiments of the present invention, the invention is not limited to such embodiments.

The present invention provides a fluorosulfonyl carbonate compound represented by the following Formula 1.

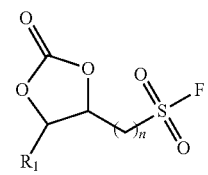

[Formula 1]

where, $R_1$ is hydrogen, a halogen atom, an unsubstituted $C_1$-$C_{10}$ alkyl group, or a halogen-substituted $C_1$-$C_{10}$ alkyl group; and n is an integer of 1 to 5.

In the above formula of the present invention, the symbol of hydrogen is omitted except for a special kind of bond.

In an embodiment of the present invention, the compound may preferably be 4-[(fluorosulfonyl)methyl]-1,3-dioxolan-2-one, wherein $R_1$ is hydrogen and n is 1.

The present invention also provides a method of preparing a fluorosulfonyl carbonate compound represented by the above Formula 1. Specifically, the method comprises the following steps:

(S1) preparing a compound represented by the following Formula 3 from the compound represented by the following Formula 2;

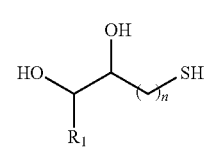

[Formula 2]

(S2) preparing a compound represented by the following Formula 4 from the compound represented by the following Formula 3;

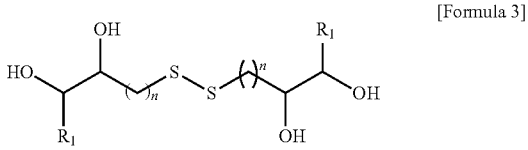

[Formula 3]

(S3) preparing a compound represented by the Formula 1 from the compound represented by the following Formula 4.

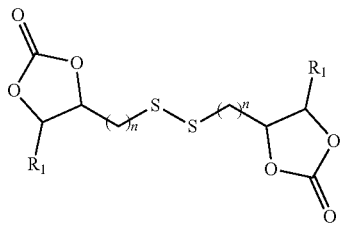

[Formula 4]

where, $R_1$ is each independently hydrogen, a halogen atom, an unsubstituted $C_1$-$C_{10}$ alkyl group, or a halogen-substituted $C_1$-$C_{10}$ alkyl group; and n is an integer of 1 to 5.

At this time, the step (S3) may further comprise preparing a compound represented by the following Formula 5 from the compound represented by the Formula 4; and (S4) preparing the compound represented by the Formula 1 from the compound represented by the following Formula 5.

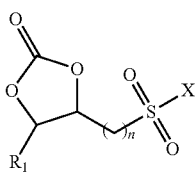

[Formula 5]

where, $R_1$ is each independently hydrogen, a halogen atom, an unsubstituted $C_1$-$C_{10}$ alkyl group, or a halogen-substituted $C_1$-$C_{10}$ alkyl group; X is Cl, Br or I; and n is an integer of 1 to 5.

Each step is reviewed in detail below.

Step (S1): Oxidation Reaction

In the preparation method of the present invention, the step (S1) is a step of preparing the compound of the Formula 3 by a reaction of oxidizing the thiol group of the compound of the Formula 2.

The step (S1) may be carried out in the presence of an oxidizing agent capable of oxidizing thiol groups. In addition, preferably, hydrogen peroxide ($H_2O_2$) may be used.

The step (S1) may also be carried out in the presence of an organic solvent commonly used in oxidation reactions. Preferably, ethyl acetate, methyl chloride, or $C_1$-$C_5$ alcohol may be used, and more preferably, methanol may be used.

In addition, the reaction of the step (S1) may be carried out at 10 to 50° C., preferably at 20 to 40° C., and more preferably at 25 to 35° C.

In addition, according to a preferred embodiment of the present invention, the step (S1) may further include a crystallization step.

The solvent used in the crystallization step is preferably methanol, isopropanol, and isopropyl ether.

Step (S2): Cyclization Reaction

In the preparation method of the present invention, the step (S2) is a step of preparing the compound of the Formula 4 by subjecting the compound of the Formula 3 to a cyclization reaction.

In a preferred embodiment of the invention, the reaction of the step (S2) is carried out as a cyclization reaction between the dihydroxyl group of the compound of formula 3 and phosgene in the presence of bis(trichloromethyl) carbonate (i.e. triphosgene).

In addition, the step (S2) may be selected from, for example, but not limited to, carbonyl chloride (i.e., phosgene), bis(trichloromethyl) carbonate (e.g., triphosgene), carbonyl bromide, bis halo formate, diphenylcarbonate, dimethylcarbonate, diethylcarbonate, carbon dioxide ($CO_2$), di-2-pyridinolcarbonate, and combinations thereof.

The step (S2) may also be carried out in the presence of an organic solvent commonly used in the cyclization reaction. Preferably, dichloromethane, dichloroethane, chloroform, methanol, ethanol, dioxane, ethylene glycol, acetonitrile, tetrahydrofuran, toluene, or dimethylformamide can be used, and more preferably tetrahydrofuran can be used.

The step (S2) may also be carried out in the presence of a base, in particular an organic base. Preferably, any one or more selected from the group consisting of triethylamine, 1-methylimidazole, pyrrolidine, imidazole, and morpholine can be used, and more preferably, triethylamine can be used.

In addition, the reaction of the step (S2) may be carried out at −10 to 35° C., preferably at 25 to 30° C.

Further, according to a preferred embodiment of the present invention, the step (S2) may further include a crystallization step.

The solvent used in the crystallization step is preferably ethanol and tetrahydrofuran.

Step (S3)

Step (S3-1): Fluorination Reaction

In the preparation method of the present invention, the step (S3) is a step of preparing the compound of Formula 1 by subjecting the compound of the above Formula 4 to a fluorination reaction. In this case, the method may be carried out by directly preparing the compound of Formula 1 without preparing the compound of Formula 5.

The step (S3) may be carried out in the presence of an electrophilic fluorinating agent, which is preferably selected from the group consisting of Selectfluor® (1-(Chloromethyl)-4-fluoro-1,4-diazabicyclo[2.2.2]octane-1,4-diium ditetrafluoroborate), and N-fluorobenzenesulfonimide, and in particular, a Selectfluor may be preferably used.

Step (S3-2): Oxidation and Halogenation Reaction

In the preparation method of the present invention, the step (S3-2) may be carried out by subjecting the compound of the Formula 4 to an oxidation and halogenation reaction to prepare the compound represented by the Formula 5.

In the reaction in the step (S3-2), any one or more selected from the group consisting of the oxidizing agents such as trimethylsilyl chloride (TMSC1), sodium hypochlorite (NaOCl), potassium peroxy monosulfate (Oxone), trichloroisocyanuric acid (TCCA), Cyanuric chloride, N-bromosuccinimide (NBS), N-chlorosuccinimide (NCS), and 1,3-dichloro-5,5-dimethylhydantoin (DCDMH) may be used, and more preferably, 1,3-dichloro,5,5-dimethylhydantoin may be used.

The reaction of step (S3) may be carried out in the presence of water, an organic solvent, and an organic acid. The organic solvent may be carried out under any one or more solvents selected from the group consisting of water, dichloromethane, dichloroethane, chloroform, tetrahydrofuran, and acetonitrile, and the organic acid may be hydrogen bromide (HBr), hydrogen chloride (HCl), sulfuric acid ($H_2SO_4$), ammonium nitrate ($NH_4NO_3$), or acetic acid. Preferably, acetonitrile and acetic acid are used.

In addition, the step (S3) may be carried out at 0 to 30° C., and preferably an oxidation and/or chlorination reaction may be carried out at 0 to 15° C.

In addition, according to a preferred embodiment of the present invention, the step (S3) may further include a crystallization step.

The solvent used in the crystallization step is preferably chloroform and water.

Step (S4): Fluorination Reaction

In the preparation method of the present invention, the step (S4) is a step of preparing the compound of the Formula 1 through a fluorination reaction from the Formula 5.

In the reaction in the step (S4), any one or more selected from the group consisting of potassium fluoride (KF), potassium difluoride ($KHF_2$), Selectfluor, hydrofluoric acid (HF), cesium fluoride (CsF), and N-fluorobenzenesulfonimide (NFSI) may be used, and potassium difluoride ($KHF_2$) may be preferably used.

In addition, the reaction of step (S4) is carried out in the presence of water for a saturated potassium difluoride ($KHF_2$) aqueous solution.

In addition, the step (S4) may be carried out using a solvent commonly used for the fluorination reaction. Preferably, dichloromethane, dichloroethane, chloroform, tetrahydrofuran, and acetonitrile can be used. More preferably, acetonitrile can be used.

In addition, the step (S4) may be carried out at 0 to 30° C., preferably at 5 to 25° C.

In addition, according to a preferred embodiment of the present invention, the step (S4) may further include a crystallization step. The solvent used in the crystallization step is preferably isopropanol.

Since the method of preparing a fluorosulfonyl carbonate compound of the present invention is carried out as a simple and mild reaction method and the fluorosulfonyl carbonate compound can be produced in high yield with little by-product, the method is suitable for mass preparation.

When the fluorosulfonyl group-containing carbonate compound represented by the general Formula 1 of the present invention is contained as an electrolyte additive, it is possible to effectively improve the efficiency of the lithium ion secondary battery.

In an embodiment of the present invention, the electrolyte additive may be contained in an amount of 0.01 to 20 parts by weight based on 100 parts by weight of the total electrolyte. Preferably, the amount of the electrolyte additive may be 0.1 to 10 parts by weight based on the total amount of the electrolyte. If the content of the electrolyte additive is less than 0.1 part by weight, the effect of improving the storage characteristics and the lifespan characteristics of the lithium secondary battery is insignificant, and if the content of the electrolyte additive is more than 10 parts by weight, a problem of increasing resistance may occur.

In an embodiment of the present invention, the electrolyte additive may further contain at least one selected from the group consisting of vinylene carbonate, fluoroethylene carbonate, succinonitrile, adiponitrile, vinylethylenecarbonate, lithiumdifluorodioxalatophosphate, lithiumtetrafluoroox- alattophosphate, Lithiumdifluorooxalatoborate, lithium difluorophosphate, propenesultone, propanesultone and ethylenesulfate. Such additives may be contained in an amount of 0.1 to 10 parts by weight based on 100 parts by weight of the total electrolyte. By being included in the above range, the electrochemical performance of the electrolyte can be improved without deteriorating the battery performance.

The present invention also provides an electrolyte for a secondary battery containing the electrolyte additive.

The present invention further provides an electrolyte for a secondary battery, including: a lithium salt; a nonaqueous solvent; and an electrolyte additive for the secondary battery containing a compound represented by the following general Formula 1.

[Formula 1]

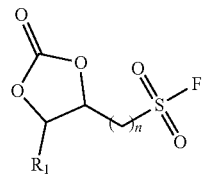

where, $R_1$ is each independently hydrogen, a halogen atom, an unsubstituted $C_1$-$C_{10}$ alkyl group, or a halogen-substituted $C_1$-$C_{10}$ alkyl group; and n is an integer of 1 to 5.

In an embodiment of the present invention, the lithium salt may be a material that acts as a source of lithium ions in the secondary battery to enable a basic operation of the lithium secondary battery, and serves to promote movement of lithium ions between a positive electrode and a negative electrode. Examples of such lithium salt may be one or more selected from the group consisting of $LiPF_6$, $LiBF_4$, $LiSbF_6$, $LiAsF_6$, $LiN(SO_2C_2F_5)_2$, $Li(CF_3SO_2)_2N$, $LiN(SO_3C_2F_5)_2$, $LiC_4F_9SO_3$, $LiClO_4$, $LiAlO_2$, $LiAlO_4$, $LiAlCl_4$, $LiN(C_xF_{2x+1}SO_2)(C_yF_{2y+1}SO_2)$ (where, x and y are natural numbers), LiCl, and LiI.

A concentration of the lithium salt is preferably used within the range of 0.1 M to 2.0 M.

Examples of the non-aqueous solvent to be used in the electrolyte of the present invention include linear carbonates, cyclic carbonates, linear carboxylic acid esters, cyclic carboxylate esters, linear ethers, cyclic ethers, organophosphorus compounds, organosulfur compounds, and the like. These compounds may be used independently or in combination of plural kinds thereof.

Examples of the linear carbonate include dimethyl carbonate, ethyl methyl carbonate, diethyl carbonate, methyl propyl carbonate, ethyl propyl carbonate, and the like. Examples of the cyclic carbonate include ethylene carbonate, propylene carbonate, vinylene carbonate, 1,2-butylene carbonate, 2,3-butylene carbonate, and the like.

Examples of the linear carboxylic acid ester include methyl acetate, ethyl acetate, propyl acetate, butyl acetate, methyl propionate, ethyl propionate, propyl propionate, and the like. Examples of the cyclic carboxylic acid ester include γ-butyrolactone, γ-valerolactone, δ-valerolactone, and the like.

Examples of the linear ether include dimethoxymethane, diethoxymethane, 1,2-dimethoxyethane, 1-ethoxy-2-methoxyethane, 1,3-dimethoxypropane, and the like. Moreover, Examples of the cyclic ether include tetrahydrofuran, 2-methyltetrahydrofuran, 3-methyltetrahydrofuran, and the like.

Examples of the organophosphorus compound include phosphoric acid esters such as trimethyl phosphate, triethyl phosphate, and triphenyl phosphate, phosphorous acid esters of trimethyl phosphite, triethyl phosphite, triphenyl phosphite, trimethyl phosphine oxide, and the like. Examples of the organic sulfur compound include 1,3-propane sultone, 1,4-butane sultone, methyl methanesulfonate, sulfolane, sulfolene, dimethyl sulfone, ethyl methyl sulfone, methyl phenyl sulfone, ethyl phenyl sulfone, and the like.

These compounds used as the non-aqueous solvent may have a substituent or may be compounds in which an oxygen atom is substituted with a sulfur atom. Examples of the substituent include halogen atoms such as a fluorine atom, a chlorine atom, and a bromine atom.

The electrolyte for a secondary battery of the present invention can be produced by mixing and stirring a non-aqueous solvent, a lithium salt, and the electrolyte additive for the secondary battery, and at this time, a known electrolyte additive commonly used for an electrolyte can be further mixed.

The present invention also provides a secondary battery including the electrolyte for a secondary battery.

The secondary battery is preferably a lithium secondary battery including a lithium-metal secondary battery, a lithium ion secondary battery, a lithium polymer secondary battery, a lithium ion polymer secondary battery, or the like.

The secondary battery of the present invention may contain, as components, for example, a positive electrode containing a positive electrode active material; a negative electrode containing a negative electrode active material, a separation membrane disposed between the positive electrode and the negative electrode, and the electrolyte for the secondary battery described above.

The secondary battery of the present invention can be produced according to a conventional method known in the related art, and in the present embodiment, the secondary battery may be produced by providing a separation membrane disposed between a negative electrode and a positive electrode active material, and the positive electrode, followed by injecting an electrolyte containing the electrolyte additive containing the fluorine- and sulfonyl group-containing carbonate compound according to the present invention.

As the positive electrode active material, one or more selected from the group consisting of cobalt, manganese, iron, aluminum and nickel; or a lithium composite metal oxide can be used. The metal mixture used for the positive electrode active material may be provided in various ways, and may further contain, in addition to these metals, a component selected from the group consisting of K, Na, Ca, Sn, V, Ge, Ga, B, As, Zr, Cr, Sr, and rare earth elements.

As the negative electrode active material, it is possible to use crystalline or amorphous carbon; a carbon-based negative electrode material of a carbon composite; a burned organic polymer compound; carbon fiber; a tin oxide compound; lithium metal; or a lithium alloy. For example, there are lithium adsorbent materials such as lithium metal or lithium alloy carbon, petroleum coke, activated carbon, graphite, graphitized carbon or other carbon, and non-limiting examples of negative electrode current collectors include foils made of copper, gold, nickel, copper alloys or combinations thereof.

The separator is to prevent a short circuit between the positive electrode and the negative electrode, polypropylene-based, polyethylene-based, polyolefin-based porous separators; microporous films; webs; and nonwoven fabrics may be used.

The lithium secondary battery electrolyte containing the electrolyte additive containing the fluorosulfonyl carbonate compound of the present invention and the lithium secondary battery produced using the same have excellent lifespan characteristics, storage characteristics, and thermal stability, and exhibit high charge-discharge efficiency, and thus have an effect of improving battery performance.

The fluorosulfonyl carbonate compound of the present invention can also be variously utilized as a raw material or an intermediate of fine chemicals, pharmaceuticals and polymer materials, etc. Preferably, the fluorosulfonyl carbonate compound can be used as an important intermediate and synthesis unit in the synthesis of pharmaceuticals.

The construction and action of the present invention will be described in more detail below by way of preferred embodiments of the invention. Here, these are given as preferred examples of the present invention and cannot be construed in any sense as limiting the invention thereto.

EXAMPLES

Example 1: Preparation of 4-[(fluorosulfonyl)methyl]-1,3-dioxolan-2-one

Reagents and solvents which will be mentioned below were commercially purchased from Alfa Aesar, TCI, unless otherwise specified, and $^1$H and $^{19}$F NMR were measured using a Digital AVANCE III 400 MHz Spectrometer manufactured by Bruker.

Step 1: Preparation of bis(2,3-dihydroxypropyl)disulfide

Alpha-thioglycerol (20.0 g) was dissolved in 40 mL of methanol and stirred, then an internal temperature was cooled to 0 to 5° C., and when the cooling was completed, hydrogen peroxide (35%) (10.8 g) was slowly added dropwise. After completion of the dropwise addition, the reaction proceeded while maintaining the internal temperature at 30 to 40° C., and when the reaction was completed, the solvent was removed through concentration under reduced pressure. Isopropanol and isopropyl ether were added to the concentrated residue, stirred at the internal temperature of 0 to 5° C. for 1 hour, and filtered. The filtered crystals were vacuum dried to obtain 20.0 g of bis(2,3-dihydroxypropyl)disulfide (yield: 100%).

$^1$H-NMR (400 MHz, CD$_3$OD): δ (ppm) 3.84~3.89 (m, 2H), 3.53~3.62 (m, 4H), 2.93~2.97 (m, 2H), 2.75~2.80 (m, 2H).

Step 2: Preparation of bis-(1,3-dioxolan-2-one)disulfide

Bis(2,3-dihydroxypropyl) disulfide (20.0 g) is dissolved in 300 mL of tetrahydrofuran and stirred, then an internal temperature is cooled to 0 to 5° C., and when the cooling is complete, bis-trichloromethyl carbonate (28.0 g) was added slowly. The internal temperature was maintained at 0 to 5° C., and triethylamine (37.8 g) was slowly added dropwise. After completion of the dropwise addition, the reaction proceeded while maintaining the internal temperature at 20 to 30° C., and when the reaction was completed, ethyl acetate and water were added to extract the organic layer. Magnesium sulfate was added to an organic layer to remove moisture, and the solvent was removed through concentration. Tetrahydrofuran and ethanol were added to the concentrated residue, stirred at the internal temperature of 0 to 5° C. for 30 minutes, and filtered. The filtered crystals were vacuum dried to obtain 25.0 g of bis-(1,3-dioxolan-2-one) disulfide (yield: 100%).

$^1$H-NMR (400 MHz, CDCl$_3$): δ (ppm) 4.98~5.05 (m, 1H), 4.62~4.67 (m, 1H), 4.27~4.34 (m, 1H), 3.04~3.23 (m, 2H).

Step 3: Preparation of 4-[(fluorosulfonyl)methyl]-1,3-dioxolan-2-one

Bis-(1,3-dioxolan-2-one)disulfide (1.0 mmol) was dissolved in 10 mL of acetonitrile and 1 mL of water, Select Fluor (2.3 g) was added, and the mixture was stirred under reflux for 12 hours. After completion of the reaction, a temperature was lowered to room temperature, and water and ethyl acetate were added to extract the organic layer. Magnesium sulfate was added to the organic layer to remove moisture, concentrated to remove the solvent, and vacuum dried to obtain 4-[(fluorosulfonyl)methyl]-1,3-dioxolan-2-one in 90% yield.

Examples 2 to 4: Modification of Step 3

*149 1,3-dichloro-5,5-dimethyl hydantoin (DCDMH), N-chlorosuccinimide (NCS), and trimethylsilylchloride (TMSC1), as oxidizing agents, respectively were added to bis-(1,3-dioxolan-2-one)disulfide prepared in Step 2 of Example 1 to prepare 4-[(chlorosulfonyl)methyl]-1,3-dioxolane-2-one as follows.

Example 2: Addition of 1,3-dichloro-5,5-dimethyl hydantoin (DCDMH)

Bis-(1,3-dioxolan-2-one)disulfide (25.0 g) is dissolved in 25 mL of acetonitrile and stirred, then an internal temperature is cooled to 0 to 5° C., and when the cooling is complete, 94 mL of acetic acid and 63 mL of water were added. The internal temperature was maintained at 0 to 5° C., and 1,3-dichloro-5,5-dimethyl hydantoin (DCDMH) was added slowly. After the completion of the addition, the reaction proceeded for 30 minutes while maintaining the internal temperature at 0 to 5° C., and then the reaction proceeded for 30 minutes while maintaining the internal temperature at 20 to 30° C. When the reaction was completed, dichloromethane and water were added to extract the organic layer. Magnesium sulfate was added to the organic layer to remove moisture, and the solvent was removed through concentration. 300 mL of chloroform was added to the concentrated residue, stirred at the internal temperature of 0 to 5° C. for 10 minutes, and then filtered, and the obtained solid compound was added to 300 mL of water at the internal temperature of 0 to 5° C., stirred for 10 minutes, and then filtered. The filtered crystals were vacuum dried to obtain 35.0 g of 4-[(chlorosulfonyl)methyl]-1,3-dioxolan-2-one (yield: 92.0%).
$^1$H-NMR (400 MHz, CD$_3$CN): δ (ppm) 5.30~5.36 (m, 1H), 4.67~4.71 (m, 1H), 4.44~4.50 (m, 1H), 4.26~4.31 (m, 2H)

4-[(chlorosulfonyl)methyl]-1,3-dioxolan-2-one prepared in Example 2 above was prepared by the method of Step 4 below as the final product, 4-[(fluorosulfonyl) methyl]-1,3-dioxolane-2-one.

Step 4: Preparation of 4-[(fluorosulfonyl)methyl]-1,3-dioxolan-2-one

Potassium difluoride (KHF$_2$, 31.3 g) was dissolved in 85.0 mL of water and stirred. 85.0 mL of acetonitrile and 35.0 g of 4-[(chlorosulfonyl)methyl]-1,3-dioxolan-2-one were added to cold saturated potassium difluoride, and stirred vigorously. When the reaction was completed, ethyl acetate and water were added to extract an organic layer. Magnesium sulfate was added to the organic layer to remove moisture, and the solvent was removed through concentration. Isopropyl ether was added to the concentrated residue, stirred at the internal temperature of 0 to 5° C. for 30 minutes, and filtered, and then the obtained solid compound was vacuum-dried to obtain 24.0 g of 4-[(fluorosulfonyl)methyl]-1,3-dioxolan-2-one (yield: 76.0%).
$^1$H-NMR (400 MHz, CD$_3$CN): δ (ppm) 5.20~5.27 (m, 1H), 4.65~4.70 (m, 1H), 4.26~4.30 (m, 1H), 4.12~4.18 (m, 1H), 4.00~4.07 (m, 1H), $^{19}$F-NMR: δ (ppm) 59.26

Example 3: Addition of N-chlorosuccinimide (NCS)

Bis-(1,3-dioxolan-2-one)disulfide (1.0 mmol) was dissolved in 10 mL of acetonitrile and 1 mL of water and stirred at room temperature for 1 hour. After completion of the reaction, a temperature was lowered to room temperature, and water and ethyl acetate were added to extract an organic layer. Magnesium sulfate was added to the organic layer to remove moisture, concentrated to remove the solvent, and vacuum dried to obtain 4-[(chlorosulfonyl)methyl]-1,3-dioxolan-2-one in 85% yield.

Example 4: Addition of trimethylsilylchloride (TMSC1)

After dissolving bis-(1,3-dioxolan-2-one)disulfide (1.0 g) in 20 mL of acetonitrile, ammonium nitride (3.0 g) and trimethylsilyl chloride (4.1 g) were added and raised to 50° C. to react for 3 hours. After completion of the reaction, a temperature was lowered to room temperature, and water and ethyl acetate were added to extract an organic layer. Magnesium sulfate was added to the organic layer to remove moisture, concentrated to remove the solvent, and vacuum dried to obtain 4-[(chlorosulfonyl)methyl]-1,3-dioxolan-2-one in 53% yield.

Comparative Examples 1 and 2

Oxone (monopersulfate compound) and cyanuric chloride, as oxidizing agents, respectively, were added to the bis-(1,3-dioxolan-2-one)disulfide prepared in step 2 of Example 1 and 4-[(chlorosulfonyl)methyl]-1,3-dioxolan-2-one was attempted to be prepared, but the product was very small or not produced.

Comparative Example 1: Addition of Oxone (Monopersulfate Compound)

Bis-(1,3-dioxolan-2-one)disulfide (1.0 g) was dissolved in 20 mL of tetrahydrofuran and 2 mL of water, Oxone (2.3 g) and sodium chloride (0.44 g) were added thereto, and stirred at room temperature. However, the desired product was not obtained through the reaction.

Comparative Example 2: Addition of Cyanuric Chloride

Bis-(1,3-dioxolan-2-one)disulfide (1.0 g) was dissolved in 18 mL of acetonitrile and 0.17 mL of water, and then tetrabutylammonium chloride (4.17 g) was added. After that, a small amount of cyanuric chloride (0.35 g) was added at 0° C., and the temperature was raised to 50° C., followed by a reaction for 3 hours. The reaction mostly remained as a starting material, and the product was found to be very small up to 5%. This was confirmed to be because the carbonate group was unstable under the reaction conditions and was broken into an alcohol form.

Example 5: Preparation of Electrolyte and Lithium Secondary Battery

LiPF$_6$ was added to an organic solvent in which ethylene carbonate (EC) and propylene carbonate (PC) were mixed in a weight ratio of 1:1 so as to have a concentration of 1 M, and then, 4-[(fluorosulfonyl)methyl]-1,3-dioxolan-2-one was added to the prepared solution was added so as to be 5% by weight based on the total weight of the electrolyte to prepare an electrolyte. A lithium secondary battery was manufactured by assembling a 1.3 Ah pouch battery using the electrolyte thus prepared as an electrolyte, using LiCoO$_2$ as a positive electrode active material, and using natural graphite as a negative electrode active material in a conventional manner.

The invention claimed is:

1. A fluorosulfonyl carbonate compound represented by the following Formula 1,

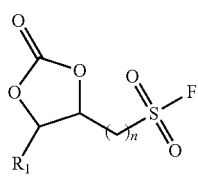

[Formula 1]

where, R$_1$ is hydrogen, a halogen atom, an unsubstituted C$_1$-C$_{10}$ alkyl group, or a halogen-substituted C$_1$-C$_{10}$ alkyl group; and n is an integer of 1 to 5.

2. The compound of claim 1, wherein R$^1$ is hydrogen, and n is 1.

3. A method of preparing a fluorosulfonyl carbonate compound represented by the following Formula 1, the method comprising the followings steps:

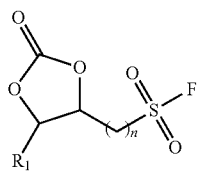

[Formula 1]

(S1) preparing a compound represented by the following Formula 3 from a compound represented by the following Formula 2;

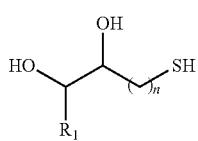

[Formula 2]

(S2) preparing a compound represented by the following Formula 4 from the compound represented by the following Formula 3;

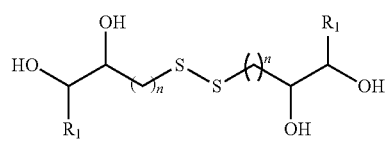

[Formula 3]

(S3) preparing the compound represented by the Formula 1 from a compound represented by the following Formula 4,

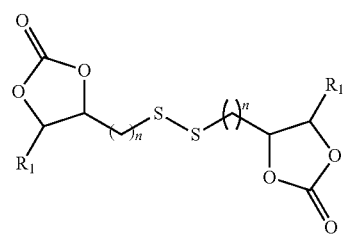

[Formula 4]

where, R$_1$ is each independently hydrogen, a halogen atom, an unsubstituted C$_1$-C$_{10}$ alkyl group, or a halogen-substituted C$_1$-C$_{10}$ alkyl group; and n is an integer of 1 to 5.

4. The method of claim 3, further comprising:
the step (S3) of preparing a compound represented by the following Formula 5 from the compound represented by the Formula 4; and
the step (S4) of preparing a compound represented by the Formula 1 from the compound represented by the following Formula 5;

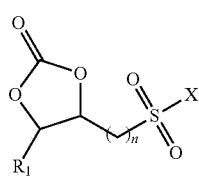

[Formula 5]

where, R$_1$ is each independently hydrogen, a halogen atom, an unsubstituted C$_1$-C$_{10}$ alkyl group, or a halogen-substituted C$_1$-C$_{10}$ alkyl group; X is Cl, Br or I; and n is an integer of 1 to 5.

5. The method of claim 3, wherein the step (S1) is carried out in the presence of an oxidizing agent.

6. The method of claim 5, wherein the oxidizing agent is hydrogen peroxide (H$_2$O$_2$).

7. The method of claim 3, wherein the step (S2) is carried out in the presence of any one or more selected from the group consisting of bis(trichloromethyl) carbonate, carbonyl chloride, carbonyl bromide, bishaloformate, diphenylcarbonate, dimethylcarbonate, diethylcarbonate, carbon dioxide, and di-2-pyridinolcarbonate.

8. The method of claim 3, wherein the step (S2) is carried out in the presence of at least one organic solvent selected from the group consisting of dichloromethane, dichloroethane, chloroform, methanol, ethanol, dioxane, ethylene glycol, acetonitrile, tetrahydrofuran, toluene, and dimethylformamide.

9. The method of claim 3, wherein the step (S3) is carried out in the presence of an electrophilic fluorinating agent.

10. The method of claim 9, wherein the electrophilic fluorinating agent is a Selectfluor or N-fluorobenzenesulfonimide.

11. The method of claim 4, wherein the step (S3) is a step of subjecting disulfide of the compound represented by the Formula 4 to an oxidation and halogenation reaction.

12. The method of claim 4, wherein the step (S3) is carried out in the presence of any one or more selected from the group consisting of 1,3-dichloro-5,5-dimethylhydantoin (DCDMH), N-chlorosuccinimide (NCS), trimethylsilylchloride (TMSCl), cyanuric chloride, sodium hypochlorite (NaOCl), potassium peroxy monosulfate (Oxone), trichloroisocyanuric acid (TCCA), and N-bromosuccinimide (NBS).

13. The method of claim 4, wherein the step (S4) is carried out in the presence of any one or more selected from the group consisting of potassium fluoride, potassium difluoride, Selectfluor, hydrofluoric acid, cesium fluoride, and N-fluorobenzenesulfonimide.

14. An electrolyte additive for a secondary battery comprising the fluorosulfonyl carbonate compound of claim 1.

15. An electrolyte comprising the electrolyte additive for the secondary battery of claim 14.

16. A lithium secondary battery comprising the electrolyte of claim 15.

17. An electrolyte additive for a secondary battery comprising the fluorosulfonyl carbonate compound of claim 2.

\* \* \* \* \*